United States Patent [19]
Yang et al.

[11] Patent Number: 5,253,981
[45] Date of Patent: Oct. 19, 1993

[54] MULTICHANNEL PUMP APPARATUS WITH MICROFLOW RATE CAPABILITY

[75] Inventors: Frank J. Yang, 20056 Karn Cir., Saratoga, Calif. 95070; Chiko Fan, Danville, Calif.

[73] Assignee: Frank Ji-Ann Fu Yang, Saratoga, Calif.

[21] Appl. No.: 847,654

[22] Filed: Mar. 5, 1992

[51] Int. Cl.⁵ .................... F04B 41/05; F04B 49/08
[52] U.S. Cl. ........................... 417/3; 417/4; 417/5; 417/18; 417/20; 417/22; 417/45; 417/53; 417/415; 210/101; 210/198.2; 210/656
[58] Field of Search ............ 417/3, 4, 5, 6, 18, 417/20, 22, 45, 53, 415; 210/198.2, 101, 656

[56] References Cited

U.S. PATENT DOCUMENTS

| | | |
|---|---|---|
| Re. 31,608 | 6/1984 | Magnussen, Jr. |
| 3,922,957 | 12/1975 | Ogle et al. |
| 3,976,400 | 8/1976 | Major |
| 4,128,476 | 12/1978 | Rock |
| 4,260,342 | 4/1981 | Leka et al. |
| 4,311,586 | 1/1982 | Baldwin et al. |
| 4,496,245 | 1/1985 | Conrad et al. ............ 210/198.2 |
| 4,566,868 | 1/1986 | Menzies ..................... 417/415 |
| 4,714,545 | 12/1987 | Bente et al. ................... 417/5 |
| 4,723,941 | 2/1988 | Thistle et al. ............... 417/415 |
| 4,728,434 | 3/1988 | Trafford |
| 4,797,207 | 1/1989 | Honganen et al. ......... 210/101 |
| 4,808,077 | 2/1989 | Kan et al. ..................... 417/45 |
| 4,874,296 | 10/1989 | Moynihan .................... 417/415 |
| 4,883,409 | 11/1989 | Strohmeier et al. ........ 210/101 |
| 4,895,500 | 1/1990 | Hök et al. ................... 417/413 |
| 4,913,624 | 4/1990 | Seki et al. .................... 417/53 |
| 4,981,597 | 1/1991 | Alllington et al. .......... 210/198.2 |
| 5,028,696 | 7/1991 | Torres et al. ................ 210/656 |
| 5,089,124 | 2/1992 | Mahar et al. ................. 417/18 |

Primary Examiner—Richard A. Bertsch
Assistant Examiner—David W. Scheuermann
Attorney, Agent, or Firm—Trask, Britt & Rossa

[57] ABSTRACT

A multichannel pump system for HPLC and other uses has a plurality of fluid pumps whose input is fed separately to at least one high pressure mixing unit downstream of the pumps and any associated items such as pulse dampeners and pressure transducers. A pump controller is connected to control each of the pumps separately in a coordinated manner to provide a plurality of operational modes. The operational modes include an isocratic mode, in which optionally the output of solvent of like composition from two or more pumps is pooled to provide increased output capacity, as well as binary, ternary, etc., gradient modes in which different solvents are selectively mixed before being applied to an analytical unit such as an HPLC column. The pump system further includes a novel linear drive pump having interchangeable piston modules providing different ranges of flow rates. The linear drive pump is capable of providing precise solvent delivery at high pressure for flow rates from 20 ml/minute down to 0.0001 ml/minute, and is particularly useful because of its microflow gradient elution capability.

20 Claims, 8 Drawing Sheets

MULTICHANNEL PUMP APPARATUS WITH MICROFLOW RATE CAPABILITY

BACKGROUND OF THE INVENTION

1. Field

The invention relates to high-pressure fluid pumping systems, and more particularly to pump systems for HPLC and other chemical and biological analytical procedures.

2. State of the Art

Fluid pumping systems for high-pressure liquid chromatography (referred to hereinafter as HPLC) and the like are well known. In HPLC, a sample is applied to the top of a column which is packed with particles of a selected size and composition, and a solvent or solvent mixture is pumped through the column. Chemical components of the sample are eluted in the solvent from the lower end of the column at different times in a manner which reflects their chemical properties and composition. For reproducibility and high analytical accuracy, HPLC requires fluid pumping which is stable and essentially pulseless (smooth flow which does not vary during fill and pump strokes), with defined precise flow rates.

Typical prior art pumps employed in these systems, as exemplified in U.S. Pat. Nos. 4,045,343 to Achener et al., Re. 31,608 to Magnussen, Jr., 4,260,342 to Leka et al., and 4,599,045 to Gordon et al., comprise a unidirectional motor driving a piston by means of a cam. Such pumps generally provide useful flow rates of between about 100 µl per minute and 10 ml per minute (microliter is abbreviated herein as "µl", and milliliter is abbreviated as "ml").

A common technique used to enhance separation of compounds by HPLC is to use two or more solvents and to vary the relative amounts of the solvents in the solvent mixture as it is being pumped through the column. This technique is often referred to as gradient separation or gradient HPLC. Formation of the gradient requires mixing of the two solvents in a controlled fashion prior to injecting the solvent mixture into the column. Typical prior art HPLC pumping systems use one of two main arrangements for mixing the solvents, as exemplified in U.S. Pat. Nos. 4,311,586 to Baldwin et al., and 4,714,545 to Bente et al. In both arrangements, the solvents are mixed together before entering the pump which pumps the mixture into the column.

A development of importance in the area of HPLC is the use of so-called "microbore" columns having an internal diameter (abbreviated herein as I.D.) of 1 millimeter or less. (See R. Scott and P. Kucera, *J. Chromatogr.* 169:51, 1979; F. Yang, *J. Chromatogr.* 236: 265, 1982; F. Yang, U.S. Pat. No. 4,483,733, (Nov. 1984); D. Ishii et al., *J. Chromatogr.* 144: 157, 1977; D. Ishii et al., *J. Chromatogr.* 185: 73, 1979; T. Takeuchi et al., *J.Chromatogr.* 238: 409, 1982.) The advantages of microbore column HPLC over conventional HPLC include reductions of up to 100-fold each in the amounts of solvent and column packing required. Such reductions bring corresponding reduction not only in the initial cost of solvent and expensive column packing material, but in the amount of solvent which must be disposed of after use. Since many of the solvents used in HPLC have toxic components, the environmental benefit of microbore HPLC vs. conventional HPLC is substantial. Additionally, there are numerous advantages for various analytical procedures (see above references).

Instrumentation for micro-bore HPLC has been developed by several LC instrument manufacturers. The typical "1.0 mm. id. micro-HPLC pump" systems presently commercially available are modified versions of conventional low pressure proportioning HPLC gradient pumps (See H. Bente, et al. U.S. Pat. No. 4,714,545 (December 1987); G. Leka et al., U.S. Pat. No. 4,260,342, (April 1981); P. Trafford, U.S. Pat. No. 4,728,434 (March 1988); P. Achener, et al., U.S. Pat. No. 4,045,343 (August 1977); J. Rock, U.S. Pat. No. 4,128,476 (December 1978); H. Magnussen, Jr. U.S. Pat. No, 4,180,375 (December 1979); H. Magnussen, Jr., U.S. Pat. No. 4,131,393, (December 1978); R. Allington, U.S. Patent No. 4,869,374 (September 1989). Such conventional systems use cam-driven pumps in which each solvent is drawn separately into the piston chamber by the fill stroke of the pump. Mixing occurs by turbulence during the fill stroke and/or by pumping the mixed fluids through a mixing unit before injecting it into the column. It is highly desirable to have the fill stroke extremely short in comparison to the pump stroke (U.S. Pat. No. 4,311,586 to Baldwin et al.). With cam-driven pumps, the desired ratio of the fill stroke to the total cycle is achieved by selecting the shape and dimensions of the cam.

However, it is difficult to dimensionally adapt such cam-driven pump designs to provide both low flow rates under high pressure and a very low fill stroke/stroke cycle ratio. As a practical matter, cam-driven pumps with the desired stroke ratios cannot be designed for flow rates lower than about 50 µl per minute. Also, cams for these low flow rates are quite large, increasing the bulk of the pump which must be used within a relatively small area crowded with other apparatus.

Therefore, the modified conventional systems referred to in the preceding paragraph for microbore applications provide a lower flow rate to individual columns either by the split-flow technique (Sj. van der Wal et al., *J. High Resolut Chromatogr. Commun.* 6: 216, 1983), or by reducing the volume of the piston chamber.

Unfortunately, such modified low pressure proportioning pump systems operate poorly at flow rates below 50 µl/min in gradient HPLC with microbore columns. There are three major problem areas. First, the sum of the system volume including proportioning valves, piston chamber, inlet check valve and interface tubings is typically five to ten time greater than the amount of solvent eluted per minute, which places a lower limit on the minimum gradient step obtainable. For typical example, there may be a 100 µl total system volume for a system operating at 10 µl per minute. In this case, it takes about ten minutes for every gradient step change. Such a large minimum step provides very poor resolution for linear gradient elution.

Second, again because of the relatively large system volume, there is a long gradient delay time. Because the mixed solvent at the outlet cavity of the proportioning valves must travel through a piston chamber having a large liquid-end volume, in addition to the above-mentioned components, the effective gradient elution of the sample components in the column is delayed a long time. A typical pump liquid end volume of 2 ml therefore causes about 200 minutes gradient delay when operated at a column elution rate of 10 µl/min.

The long delay times and the relatively large gradient steps are not only time-consuming for the user, but also allow significant diffusion of the solvents in the gradient to occur. As a result of such diffusion, the gradients are generally poorly reproducible and sample components are poorly separated (L. Snyder et al., "Reproducibility problems in gradient elution caused by differing equipment," LC-GC, Vol. 8, No. 7, p. 524, 1990).

A further disadvantage is that the gradient regeneration time is very long. A volume approximately three times that of the pump liquid end is required for purging and regeneration of the initial solvent composition. For the 2 ml liquid end volume of the previous example above, it will take 600 minutes to regenerate the initial solvent composition at a 10 l/minute elution rate.

One typical approach to alleviating these problems of cam-driven pumps at low flow rates is the split flow technique. The solvent gradient is generated at high flow rate to eliminate the problem of gradient delay. A microflow stream is then split at constant pressure from the main solvent stream and sent to the injector and column; the excess flow is usually discarded. Thus, the split-flow technique does not offer any reduction in solvent use over conventional methods. Also, because the gradient is split at constant pressure, the actual pressure in the microflow column has diminished stability and accuracy.

A further disadvantage of cam-driven pumps is that a single pump can only provide a limited range of flow rates. This is because different flow rate ranges require cams of substantially different size, and the position of the cam relative to the motor and the piston is determined by the cam dimensions. Changing the positions of the motor and piston to accommodate a cam of different size is impractical because of the sensitive alignment required in piston pumps.

An alternate approach for pumping in microbore column HPLC is the single-stroke syringe-type piston pump (M. Munk, U.S. Pat. No. 4,032,445 (June 1977), R. Brownlee, U.S. Pat. No, 4,347,131 (August 1982), R. Alligton, U.S. Pat. No. 4,775,481 (March 1988). This type of syringe pump is capable of delivering solvent at a few μl/min. However, syringe-type pumps also have significant disadvantages for microbore gradient HPLC. First, it is difficult to maintain a constant flow rate during gradient elution, due to the continuously changing flow resistance. This variation in flow resistance is believed to be a consequence of solvent composition, solvent compressibility and syringe liquid volume changes. Second, it is necessary to refill the liquid phase in the syringe piston between each analysis to minimize solvent compressibility effect and ensure good flow rate reproducibilty, but refilling of the syringe is generally slow. Third, for gradient elution multiple syringe pumps are required, and these are very costly.

Because of these and other disadvantages of available low flow rate pumping systems, the potential advantages of microbore HPLC have not been realized.

Consequently, a need remains for a simple and inexpensive pump which can provide pulseless, reproducible solvent flow under pressures of up to 10,000 psi at flow rates of 10 to 100 μl per minute or less. A need further remains for a pumping system having a greatly reduced liquid volume between the gradient mixing unit and the column injector, which can reproducibly provide gradient flows with small gradient steps and a short lead time.

Summary of the Invention

The invention comprises a fluid pumping system wherein gradient proportioning is performed at high pressure. The system includes a plurality of pumps each connected to separate reservoirs containing different fluids, wherein each pump is individually connected to pump fluid into a high pressure mixing unit. The mixing unit in turn is directly connected to output mixed fluid under pressure to one or more analytical units. Optionally but highly desirably, a pulse dampener and a pressure transducer are inserted in the flow path downstream of each fluid pump, before the inlet to the mixing unit. The disclosed pump system wherein solvent mixing takes place at high pressure downstream of the fluid pumps, dampeners and transducers, greatly reduces or eliminates the problems of gradient step size and gradient delay associated with conventional low pressure proportioning HPLC pumping systems.

The pumping system includes a pump system controller connected to separately control each of the individual pumps, thereby permitting the system to be used to form gradients composed of two, three or four solvents (termed binary, ternary and quaternary gradients, respectively). The pump controller may also be constructed to pool the outputs of fluid of similar composition from different pumps to provide increased flow rates thereof.

The invention further includes a linear drive fluid pump which is preferred for use in the pumping system. The linear drive pump has a reciprocating piston driven by a linear actuator operably connected to a bidirectional motor. A pump frame has the bidirectional motor attached at one end and a piston chamber attached at the opposite end. The piston chamber has an inlet connected to a fluid reservoir and having valve means for regulating flow of fluid from the reservoir into the chamber. An outlet from the piston chamber is connectable to a unit such as a mixer or a column injector, and includes outlet valve means for regulating the flow of fluid out of the chamber. A piston having a drive end and a fluid end has the fluid end slidably disposed in the piston chamber. Motor coupling means are operably disposed for drivingly coupling the drive end of the piston to the linear actuator.

The linear actuator reciprocates the piston along a linear axis. In a preferred embodiment, the motor coupling means includes a floating piston mount for floatingly connecting the drive end of the piston. The piston mount has a central portion which is indirectly connected to a coupling segment in the motor coupling means. This central portion carries attachment means for attaching the drive end of the piston. In the illustrated embodiment, the piston mount comprises a traveling bracket secured at opposite sides to a coupling segment which is in turn connected to the linear actuator. The terminus of the drive end of the piston is preferably configured to make point contact with the coupling segment. Preferably also, the motor coupling is constructed to allow a degree of flexibility.

In a highly preferred embodiment, the drive end of the piston and the piston chamber housing are detachably mounted to their respective mounts, thereby together constituting a module which is readily exchanged for any of a plurality of similarly constructed piston/chamber modules. Substitution of a module having different piston/chamber dimensions configures the pump for a different range of flow rates. The total range of available flow rates which can be provided by the pump is thereby dramatically increased, and ranges from 0.001 ml/minute (10 μl/minute) to 20 ml/minute.

The pumping system including the linear drive fluid pump has special advantages for use in performing microbore column chromatography. In a preferred embodiment for use with microbore columns, a gradient delay time of no more than a few minutes is desirable. Such low gradient delay times are readily obtained by minimizing the volume contained in the mixing unit, the tubing interfaces, and the injector connecting the mixing unit to the column. With a flow rate of 10 μl per minute, and minimizing the volume contained in the mixing unit and tubing interfaces to be about twice the volume contained in the column, a gradient delay time of two minutes can be achieved. The stirring means of the mixing unit is varied in shape and size to provide different mixing volumes in a single mixing unit. In a further embodiment having a cooling unit disposed to regulate the temperature of fluid in the mixing unit, the pumping system can be used for pumping supercritical fluids.

BRIEF DESCRIPTION OF THE DRAWINGS

In the figures, which depict what is presently regarded as the best mode for carrying out the invention.

DETAILED DESCRIPTION OF THE ILLUSTRATED EMBODIMENTS

Figure 1:
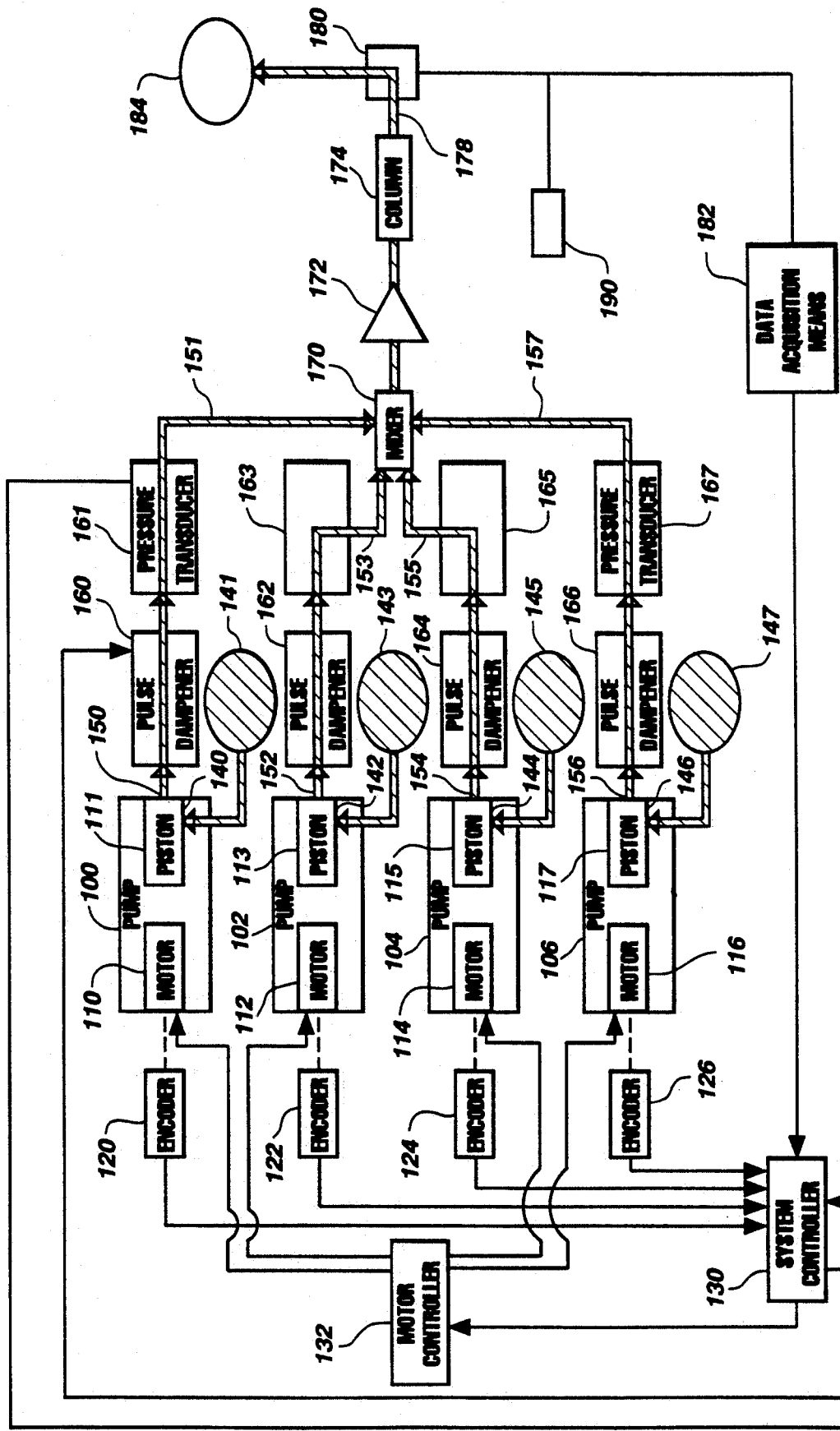
FIG. 1 is a block diagram setting forth the basic components of a multichannel pumping system having four pumping channels, with electrical communication indicated by a solid line, mechanical associations by a dashed line, and fluid flow shown as a hatched path.

FIG. 1 is a simplified block diagram depicting key components of a preferred embodiment of a pumping system having four individual pumps 100, 102, 104, 106. Preferred pumps for the system are the linear drive pump of FIG. 2, and are described in detail in reference thereto. However, other pumps may be substituted for the linear drive pump. For simplicity, therefore, only certain elements of the pump which are common to most piston and syringe-type pumps will be described in reference to FIG. 1.

Pumps 100, 102, 104, 106 each have a respective motor 110, 112, 114, 116, and a respective piston unit 111, 113, 115, 117. Each of motors 110, 112, 114, 116 is in electrical communication with a respective encoder 120, 122, 124, 126, which in turn communicate with pump system controller 130, embodied here as a personal computer. Encoders 120, 122, 124, 126 detect the rotation of their respective motors 110, 112, 114, 116, and provide rotation signals reflective thereof to pump system controller 130, which interprets the speed and position of the pump piston from the rotation signals. In the working embodiment, encoders 120, 122, 124, 126 are selected to be optical encoders integrally mounted to the individual motors. Pump system controller includes a standard digital motion control microprocessor (not shown); operation of the system controller will be described in greater detail later herein.

A motor controller 132 is connected to system controller 130 to receive motor control signals therefrom, which it then converts to motor operation signals. Motor controller 132 is further connected to send the motor operation signals to individual motors 110, 112, 114, 116.

Figure 2:
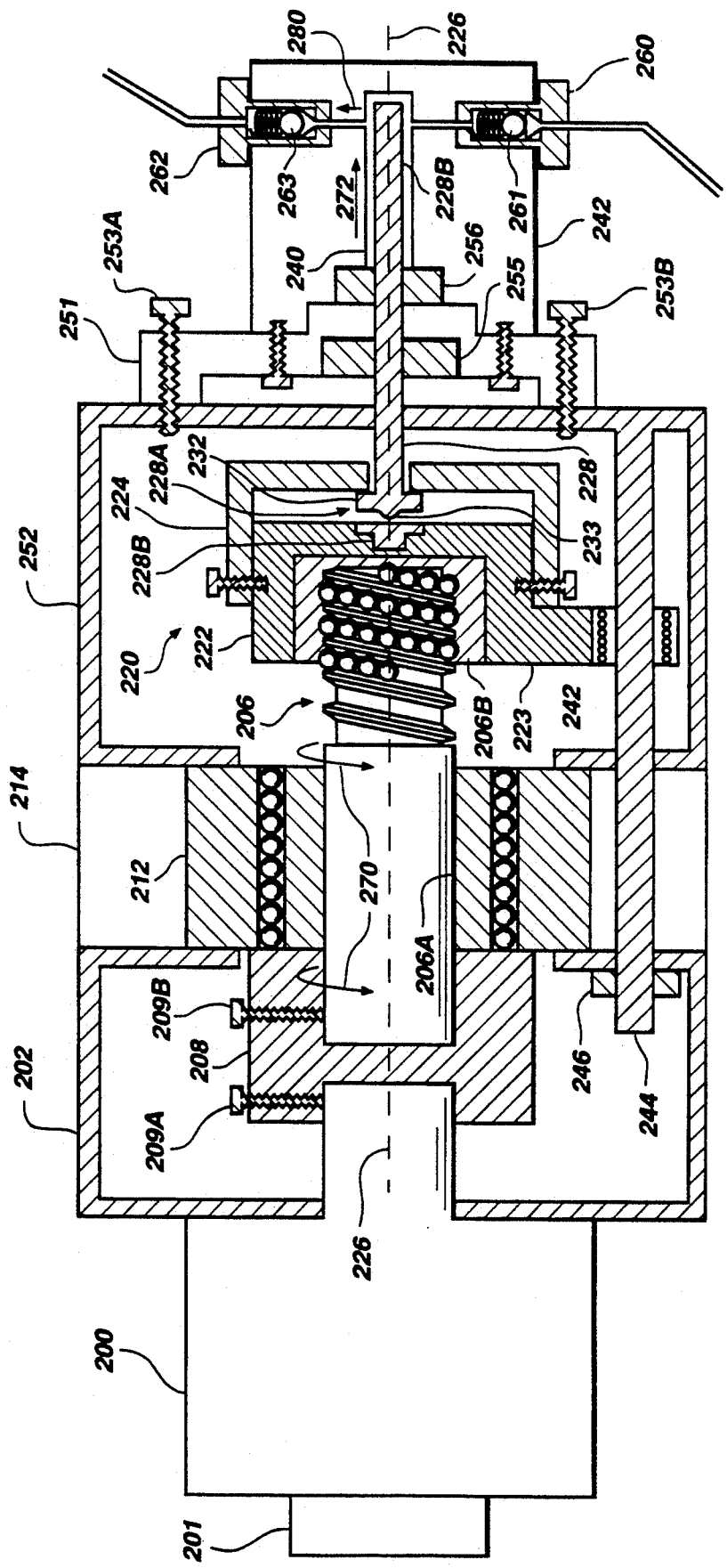
FIG. 2 is a cross sectional view of a preferred embodiment of the linear drive fluid pump with the piston in an extended position.

Piston units 111, 113, 115, 117 each comprise a piston or plunger connected to be driven by the corresponding motor 110, 112, 114, 116, and operably disposed for reciprocating movement in a piston chamber (not shown; see FIG. 2 for an example). Each of piston units 111, 113, 115, 117 is connected by means of a respective inlet valve 140, 142, 144, 146 to receive fluid from one of respective reservoirs 141, 143, 145, 147. The individual reservoirs may contain similar or different solvents, as desired by the user. In the illustrated embodiment, inlet valves 140, 142, 144, 146 comprise check valves which open to draw fluid from the reservoir into the piston chamber when suction force exerted by the piston reaches a preset level. Alternatively, inlet valves 140, 142, 144, 146 may comprise positively controlled valves, such as conventional electrically actuated on/off valves or silicon wafer micromachined valves, connected to be operated by system controller 130.

The piston chambers of piston units 111, 113, 115, 117 further have outlet valves 150, 152, 154, 156 through which fluid received from the reservoirs is expelled into respective tubing interfaces 151, 153, 155, 157. In the illustrated embodiment, outlet valves 150, 152, 154, 156 comprise check valves which permit flow of fluid out of the piston chamber when the pressure exerted by the respective piston reaches a preset level. Alternatively, outlet valves 150, 152, 154, 156 may comprise positively controlled valves as described for inlet valves 140, 142, 144, 146.

Tubing interfaces 151, 153, 155, 157 are connected to deliver fluid pumped from respective pumps 100, 102, 104, 106 to a mixing unit 170 having suitable individual inlets (not shown). Mixing unit 170 may be either a dynamic mixer similar to the one depicted in FIGS. 4 and 5 herein, or a static type mixer such as a packed bed, as desired.

Mixing unit 170 has an outlet connected to deliver mixed fluid to solvent delivery means 172, which may be any solvent delivery means suitable for applying the mixed fluid to an analytical unit 174. In the illustrated embodiment, analytical unit 174 is an HPLC column which can be any of the following: fused-silica microbore packed column, glass-lined stainless steel microbore packed column, conventional stainless steel 1 mm, 2 mm, 4.6 mm, 1 cm, 2 cm, 5 cm, or 10 cm packed column. A conventional valve injector such as a Rheodyne injector can be used as solvent delivery means 172. However, analytical unit 174 need not be an HPLC column, but may be any other type of separation or analytic unit requiring flow of a solvent gradient.

Optionally but highly desirably, pulse dampening means 160, 162, 164, 166 are operably disposed upstream of mixing unit 170 for damping pump pulsation in tubing interfaces 151, 153, 155, 157. Suitable pulse dampening means are well-known and commercially available, for example from Hardy and Harman Tube Company. Pulse dampening means 160, 162, 164, 166 are each communicatively connected to be controlled by system controller 130 (shown for pulse dampening means 160 only, for clarity).

Optionally and preferably, pressure transducers 161, 163, 165, 167 may be respectively disposed for sensing the pressure in tubing interfaces 151, 153, 155, 157 upstream of mixing unit 170. Suitable pressure transducers are commercially available, for example the Model SP 70-E from SensoMetrics, Inc., Simi Valley, Calif. Pressure transducers 161, 163, 165, 167 are each communicatively connected to send pressure signals to system controller 130 (for clarity, this is shown for pressure transducer 161 only; transducers 163, 165, 167 are similarly connected.).

For microflow HPLC, a preferred embodiment comprises a high precision motor, pumps having 0.0625 inch diameter pistons, a pulse dampener, a pressure transducer, a micro-volume (e.g. less than 30 $\mu$l) dynamic high pressure mixer, a micro-volume internal loop injector, and a microbore column of I.D. $\leq$1 mm.

In a further embodiment, the pumping system may include detection means 180 functionally disposed for detecting chemical components in the output fluid 178 of analytical unit 174. Detection means 180 may comprise probes which detect chemical components by direct contact with the output fluid 178, spectrophotometric detectors which do not require such contact, mass spectrometers, etc., or any combination of these. Detection means 180 may be connected as shown to send data signals reflective of the chemical components via a data acquisition board 190 to system controller 130 via data acquisition means 182.

Collection means 184 is desirably connected to analytical unit 174 for collecting the fluid output 178. Collection means 184 may be configured to collect fluid output 178 in bulk, or according to known types of apparatus for collecting separate aliquots selected to isolate individual chemical components appearing in different portions of fluid output 178.

Detection means 180 may alternatively be connected to send all or selected parts of the data signals to an independent computer-based data processing unit. A further option is the provision of recorder means 190 connected to detection means 180 for recording all or selected parts of the data signals. Recorder means 184 may include a visual display of recorded data signals (not shown).

As previously mentioned, pump system controller 130 includes a motion control microprocessor. The motion control processor provides the motor control signals to motor controller 132 according to well-known principles of real-time closed-loop feedback motion control. The flow rate of each individual pump depends on the rate of piston travel, which is controllable by the motion control microprocessor in accordance with signals received from the system controller. Motor controller 132 includes a pulse-width-modulated IC chip for converting the motor control signals to the motor operation signals, which are supplied to motors 110, 112, 114, 116.

Desirably, the motion control feedback system (including the encoder) has a resolution of better than 500 steps per revolution. The preferred number of total steps per piston displacement volume is 3000 to 10000 steps when the fluid pumps of the pump system are constituted by the linear drive pump of FIG. 2. This range of steps provides capability for obtaining a minimum displacement of a 0.0625 inch diameter piston for micro-HPLC to between about 8 nanoliters (abbreviated herinafter as nl) per step and 2.5 nl per step, respectively.

In the embodiment of FIG. 1, proportioning of solvents for a mixture or a gradient is accomplished by selection of the appropriate proportional flow rates for pumps delivering the respective different solvents to the mixing unit 170. For example, if a mixed fluid containing 10% solvent A/90% solvent B is desired at an output rate of X ml/minute, then pump 100 providing solvent A is operated at a flow rate equal to 0.1X, and pump 102 providing solvent B is operated at a flow rate of 0.9X.

System controller 130 is configured to control the respective flow rates of pumps 100, 102, 104, 106 in a time-varying manner for a constant output flow rate, thereby enabling the production of a gradient output flow. (Output flow rate is defined for purposes of this application as the flow rate of the mixed fluid exiting mixing unit 170.) In a preferred embodiment, system controller 130 is further configured to include a capability of varying the output flow rate both upward and downward by appropriately varying the flow rates of individual pumps. System controller 130 is further desirably constructed to vary the output flow rate for either fixed proportional rates for flow of different solvents, or simultaneously with time variation of the proportional rates of pumps delivering different solvents.

Figure 7:
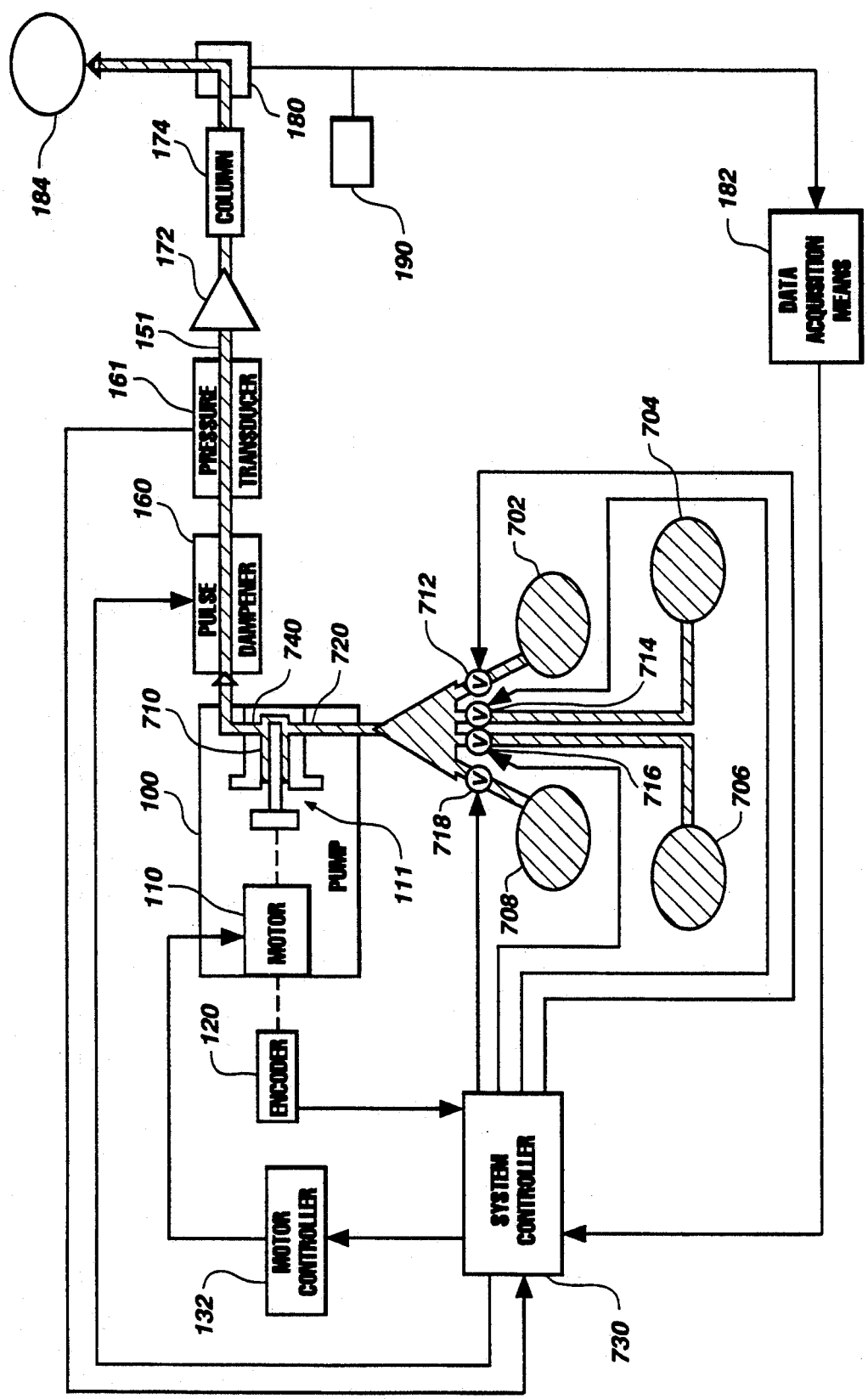
FIG. 7 is a schematic diagram of an embodiment of a linear drive fluid pump having an alternate structure for gradient proportioning.

In an alternate embodiment, mixing unit 170 of FIG. 1 is deleted and mixing is accomplished by regulation of a plurality of silicon microvalves to simultaneously deliver the desired proportions of solvents to the piston chamber itself. In such an embodiment, a single pump can replace the four pumps 100, 102, 104, 106 of the embodiment of FIG. 1. Referring to FIG. 7, a single pump 700 has a motor 701 and piston assembly 703. Pump 700 is connected to draw fluid into the piston chamber 710 from four different reservoirs 702, 704, 706, 708 through respective microvalves 712, 714, 716, 718. In the stylized depiction of FIG. 7, microvalves 712, 714, 716, 718 ar ®shown feeding into a common inlet 720 of piston chamber 710. In an alternate embodiment (not shown) piston chamber 710 may be provided with four individual microvalve-controlled inlets respectively connected to reservoirs 702, 704, 706, 708.

In either case, microvalves 712, 714, 716, 718 are each operably connected to system controller 730 to receive control signals governing their operation for metering of solvent flow. Each of microvalves 712, 714, 716, 718 is a silicon chip microvalve, which may be an on/off valve operable by direct electrical signalling, by electro-mechanical means such as a piston, or by electro-thermal means, as known in the art for silicon chip valves used in automotive fuel-injection systems (Honeywell, Inc., has developed such devices). Regardless of which valve operation mechanism is used, control signals for operation of microvalves 712, 714, 716, 718 are provided thereto by controller 130, 730, respectively, in the embodiments of FIGS. 1 and 7.

Alternatively, the silicon chip microvalves may be metering-type valves, which are constructed to provide a selectable variable effective aperture which in turn defines corresponding variable fluid transport volumes. Silicon microvalves of dimensions suitable for the embodiment of FIG. 7 may be obtained from Hedco Microengineering Laboratory at the University of Utah, Salt Lake City.

In the embodiment of FIG. 7, system controller 730 is constructed to control any user-selected combination of valves 712, 714, 716, 718 to simultaneously provide respective fluids to piston chamber 710, according to respective individual user-selected transport volumes. Mixing thus occurs within piston chamber 710, which then pumps mixed fluid through outlet 740 to the analytical unit 174 essentially as shown and described for FIG. 1. Outlet valve 740 may be a check valve or a positively-controlled valve, as described for the pump of FIG. 2. System controller 730 is also configured to control both output flow rate at outlet 740 and individual input flows at valves 712, 714, 716, 718 in a time-varying manner.

At present, the embodiment of FIG. 1 is preferred over that of FIG. 7 because commercially available silicon chip valves generally lack sufficient mechanical strength to operate at high pressures for flows in the range of ≦20 ml/minute of the apparatus of this application. However, silicon chip microvalves are being widely researched, and it is believed possible that silicon microvalves having dimensions useful in the instant invention, and of sufficient reliability and precision, will be available in the future.

The linear drive pump design depicted in FIG. 2 provides positive control of the piston in both directions. Accordingly, when pumps 100, 102, 104, 106 of FIG. 1 or pump 100 of FIG. 7 are linear drive pumps, system controllers 130, 730 are further desirably configured to control the corresponding motor(s) 110, 112, 114, 116 to have a fill stroke which is extremely short by comparison with the pump stroke. (Fill stroke refers to leftward movement of piston fluid end 228B in FIG. 2, while pump stroke refers to rightward movement of fluid end 228B).

Optionally and desirably, system controllers 130, 730 are further constructed to provide a prepressurization segment at the beginning of the pump stroke. In the prepressurization segment, there is quick compression of the solvent in the piston chamber to a given pressure that is equal or higher than the inlet pressure downstream at the HPLC column. This prepressurization segment is preferably no longer than about 50 milliseconds. With the pump controller constructed to provide a short fill stroke and a short prepressurization segment time, and further including pulse dampening means immediately downstream of the pump, the pumping system provides substantially pulsation free fluid delivery.

System controllers 130 and 730 can be further constructed to optimize the refill speed and minimize cavitation. The latter is a frequent problem in both conventional cam driven reciprocating pump systems and in syringe pump systems. In a preferred embodiment of the invented pump, cavitation is reduced by providing means for applying pressure on the order of 10 to 200 psi to the solvent reservoir which is connected to the inlet of the piston chamber. Such means for applying pressure may be either pneumatic or hydraulic, or may comprise supplying the solvent from a prepressurized reservoir.

Turning to FIG. 2, a preferred linear drive fluid pump has a motor 200 having a motor shaft 204 which is linearly connected to reciprocate a piston 228 in a chamber 240. Chamber 240 has inlet valve means 260 connectable to receive fluid from a reservoir, and outlet valve means 262 for outputting fluid under pressure. Piston 228 is preferably made of a durable, chemically resistant material. In the illustrated embodiment, piston 228 comprises a zirconium oxide ceramic.

Motor 200 is mounted on a motor bracket 202, and includes an integral optical encoder 201. Preferably, motor 200 is a high torque sensitivity DC brushless servo-motor which has a peak torque of better than 200 oz-in. However, a brushless or brush servo-motor or stepping motor may also be suitable.

A high precision ball screw 206 is coupled to motor shaft 204 through a flex-coupler 208 by means of set screws 209A, 209B (shown in profile) and 210A, 210B (shown head-on). The shank 206A of ball screw 206 passes through and is supported by a ball bearing 212 mounted in a bearing bracket 214, which is affixed bracket 202. Ball screw nut 206B is threadedly and rotatably engaged with ball screw 206 and is secured to piston mounting means generally indicated at 220.

Piston mounting means 220 includes a coupling bracket 222 attached to the ball screw nut 206B, and a piston retaining bracket 224 secured by screws to the coupling bracket. Retaining bracket 224 has a central portion 224A which is planarly displaced from coupling bracket 222 along the linear axis 226 of piston travel toward the chamber 240, and out of contact with coupling bracket 222. Retaining bracket 224 carries attachment means for attaching a piston 228, described elsewhere herein with reference to FIG. 2A. Piston mounting means 220 slides reciprocatingly within a chamber mounting bracket 252 in precise accordance with the motion of motor shaft 204.

Together, flex coupler 208, ball screw 206, and piston mounting means 220 constitute motor connection means for drivingly connecting piston 228 to motor shaft 204. When the shank 206A of the ball screw is rotated in ball screw nut 206B by the action of motor 200, piston mounting means 220 moves linearly along the axis 226, as best seen by comparing FIGS. 2 and 2B.

Figures 2A, 2B:
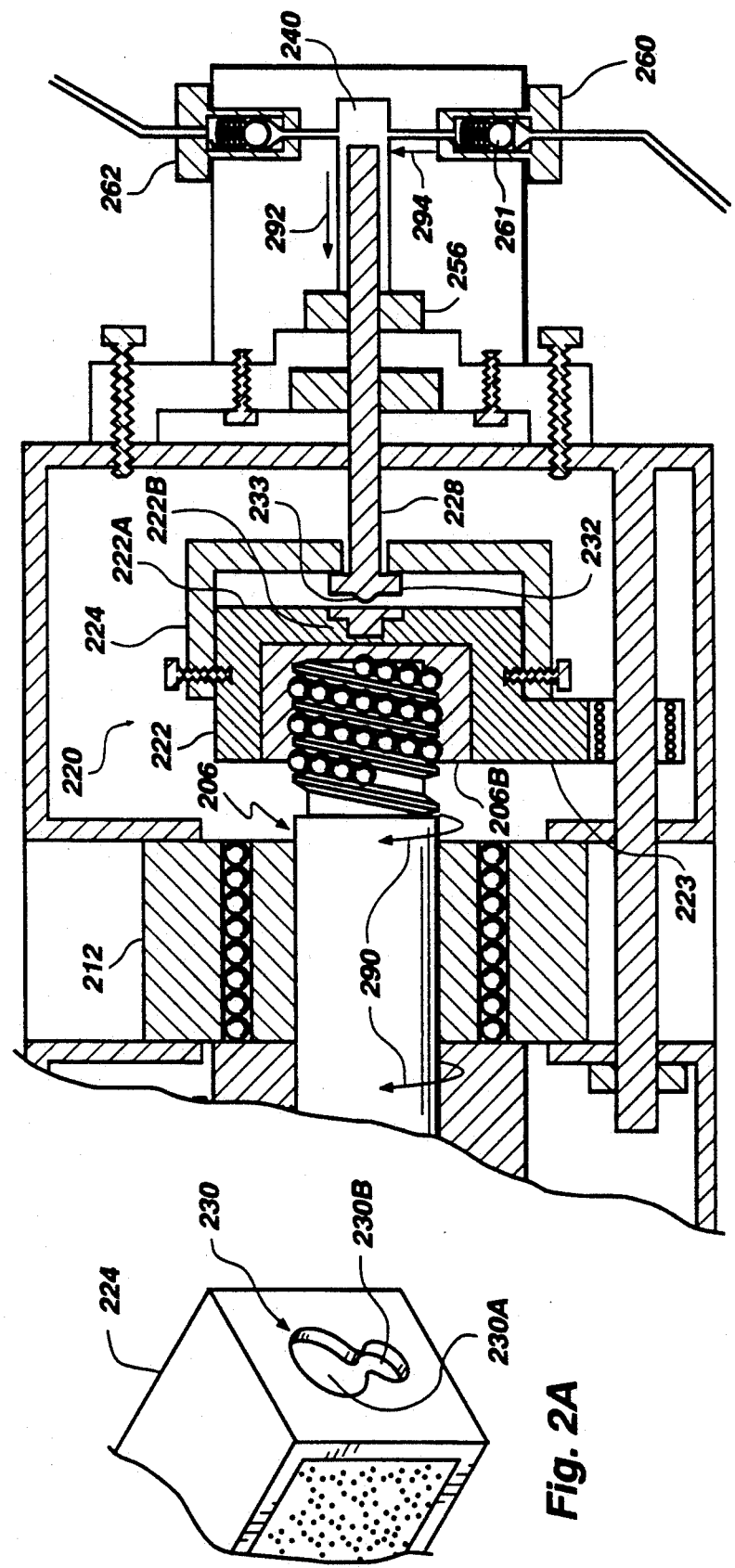
FIG. 2A is an oblique view of a preferred embodiment of a piston retaining bracket 224—of the pump of FIG. 2.
FIG. 2B is a partial cross-sectional view of the linear drive fluid pump of FIG. 2 with the piston in a retrac position.

In the working embodiment, the attachment means carried by retaining bracket 224 is a keyhole 230 in central portion 224A (FIG. 2A). Piston 228 has a drive end 228A (FIG. 2) which is correspondingly configured with a collar 232 whose dimensions are such that drive end 228A can pass through the larger diameter area 230A of keyhole 230, while collar 232 will retain drive end 228A when it is seated in the smaller diameter area 230B. In the latter configuration, piston drive end 228A is thus permitted to slide in keyhole 230 between retaining bracket 224 and coupling bracket 222. This arrangement permits piston 228 to freely float inside the piston mounting bracket, and thus facilitates trouble-free self-alignment with the chamber 240 in the attached chamber housing 250.

Piston drive end 228A is further preferably configured with a convex end surface 233. When the motor shaft 204 drives the ball screw 206 and coupling bracket 222 toward the right-hand side of FIG. 2, the forward surface 222A of the coupling bracket will contact drive end 228A of piston 228 to in turn drive the piston into the chamber 240. Forward surface 222A is desirably provided with an insert 222B of a hard durable material such as steel in the area contacted by drive end 228A of the piston. The convex surface 233 of the piston drive end further facilitates the self-alignment of piston 228 in the chamber.

In a preferred embodiment, coupling bracket 222 has a lower segment 223 having a linear ball bearing 242 which serves as a counter rotation travelling guide for the piston mounting bracket. A steel rod 244 is mounted through linear bearing 242 and secured by a nut 246 to motor bracket 202. Rod 244 may further be secured to chamber bracket 252.

Chamber 240 is formed within a chamber housing 248 affixed to a support spacer 251, which is in turn attached to chamber bracket 252. Chamber bracket 252 is in turn mounted to bearing bracket 214. Together, chamber bracket 252, bearing bracket 214 and motor bracket 202 constitute a pump frame for supporting the operating elements of the pump. In a highly preferred embodiment, chamber housing 248 is detachably mounted to chamber bracket 252, for example with thumbscrews 253A, 253B located in support spacer 251. Desirably, a guide bushing 255 made of a semiresilient material such as a Kel-F or Tefzel high strength fluorocarbon polymer is seated in the opening of chamber 240. The fluid end 228B of piston 228 is inserted through guide bushing 255 and through a high pressure seal 256 into chamber 240. Seal 256 is for maintaining pressure within chamber 240, and may comprise a spring-loaded seal available from Bal Seal Engineering Company of Tustin, Calif.

FIG. 2B is a partial view of the pump of FIG. 2 with the piston 228 in a substantially fully-retracted position. The ball screw 206 is screwed to its furthest possible extent within ball screw nut 206B, and the position of piston mounting means 220 including piston bracket 222 is shifted leftward (towards motor 200) as compared to its position in FIG. 2, while ball screw shaft 204A remains in essentially the same position relative to motor 200 in both FIGS. 2 and 2B.

Movement of piston 228 back and forth along the axis 226 causes fluid to be alternately drawn into chamber 240 from an attached reservoir (not shown) or displaced from chamber 240 through outlet 262. Inlet valve 260 includes a spring-loaded inlet check valve 261. When piston 228 is driven forward by the action of motor shaft 204 (FIG. 2), fluid in the piston chamber is expelled through a spring-loaded outlet check valve 263 into attached tubing leading to an analytical unit by way of a mixer or other desired components, as shown in FIG. 1. Conversely, when piston 228 is retracted (FIG. 2B), fluid is drawn into the piston chamber 240 through inlet 260 and check valve 261. Inlet 260 is in turn connected to the fluid reservoir. Check valves useful in the inlet 260 and outlet 262 are well known in the art and commercially available.

For solvent pumping at rates below about 30 $\mu$l/minute, a spring loaded inlet check valve operable at about 22 psi and outlet check valve operable at about 100 psi are preferred. For reproducible solvent delivery at flow rates below about 50 $\mu$l/minute in HPLC, the motor should provide reliable control of the motor speed at a few RPM. To provide a fill stroke time as short as 50 milliseconds at flow rates of 1–20 ml/minute, the motor should be capable of rotational speeds of at least about 4000 RPM.

In the illustrated preferred embodiment, chamber housing 242 and piston 228 are easily detachable from the piston frame and the piston bracket, respectively, and thereby constitute a piston module which can be easily exchanged for a module of like construction but different chamber/piston fluid end dimensions. Alternate piston modules are dimensioned to provide flow rates in a plurality of different flow rate ranges. For example, 0.0625 inch diameter pump-head and piston provides 0.0001 to 1.25 ml/min. flow rate range; 0.125 inch diameter pump-head and piston for 0.01 to 5.0 ml/min. flow rate range; and 0.25 inch diameter pump-head and piston for 0.1 to 20 ml/min. flow rate range. The corresponding volumes of chamber 240 for the above example are 25, 100, and 400 $\mu$l, respectively.

Figure 3:
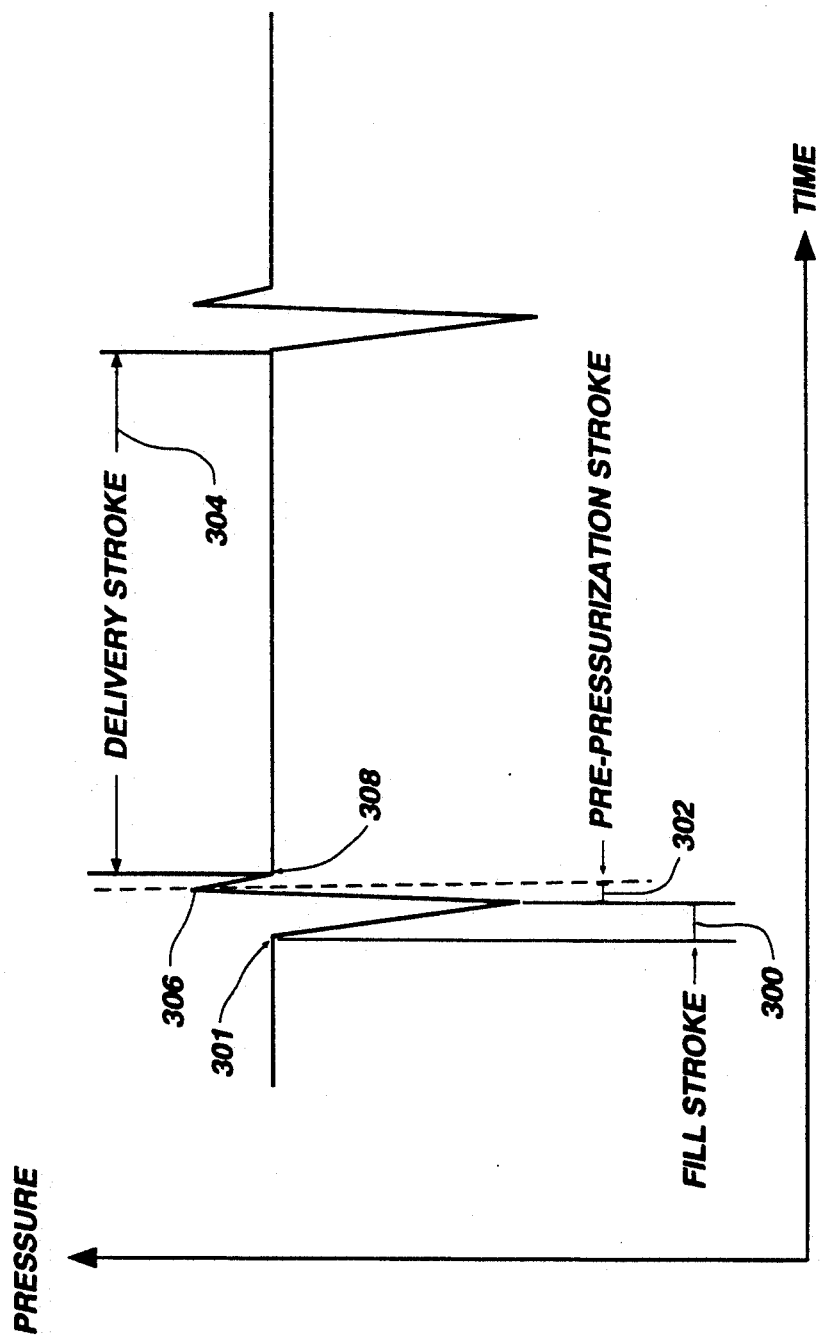
FIG. 3 is a chart illustrating the relative time spans for fill stroke, pre-pressurization stroke, and delivery stroke according to a preferred embodiment.

FIG. 3 illustrates the pressure detected within chamber 240 during a refill stroke, pre-pressurization segment, and delivery stroke cycle, for the pump of FIG. 2. The pressure within the chamber 240 drops to about 20 to 40% of the initial value at the end of a fill stroke 300 of 0.1 second duration. With a rapid pre-pressurization stroke 302 (e.g. 30 msec.) following fill stroke 300, the liquid pressure in chamber 240 reaches a value about 2 to 10% higher than the operational pressure in the delivery stroke 304. The initial pressure over-shoot 306 at the end of the pressurization cycle is allowed to decay rapidly to the operation pressure (the plateau value) during the delivery stroke. The total pulse width of the refill cycle (from the start point 301 of fill stroke 300 to the start point 308 of delivery stroke 304) of 0.1 to 0.15 second, is a high frequency pulse which can be easily dampened by a downstream on-line pulse dampener as illustrated in FIG. 1.

Figure 4:
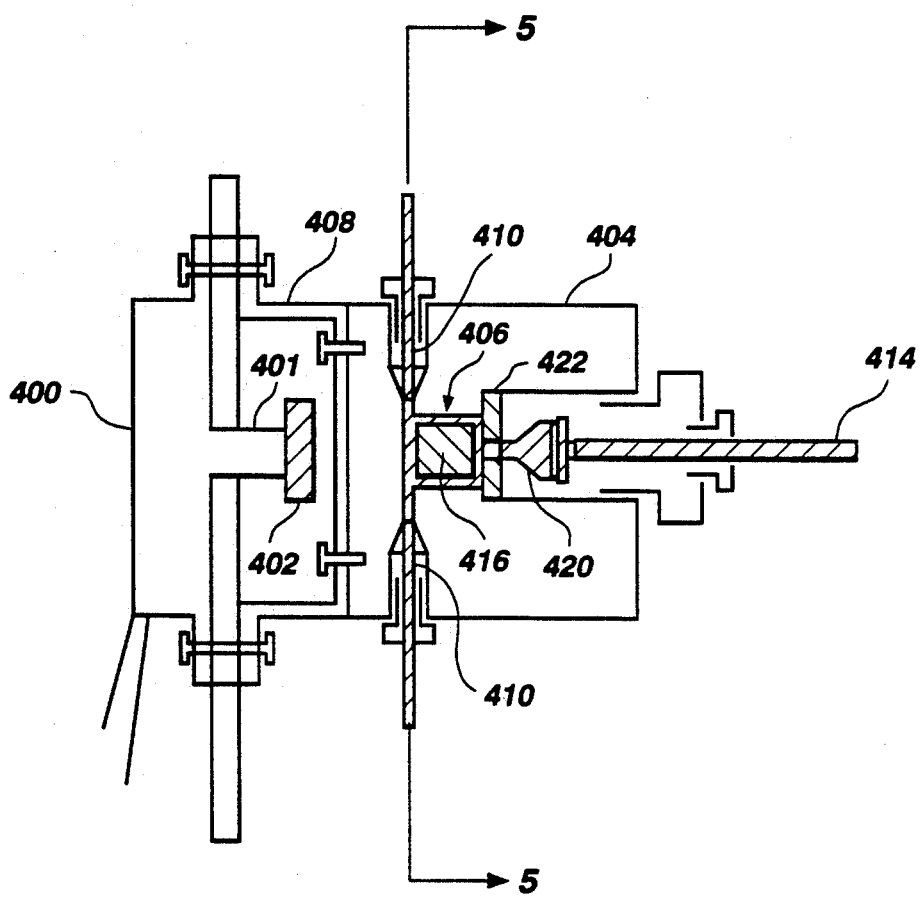
FIG. 4 illustrates coupling of the multiple fluid pumps of the embodiment of FIG. 1 inside a high pressure dynamic mixer for binary, ternary, or quarternary gradient elutions.
Figure 5:
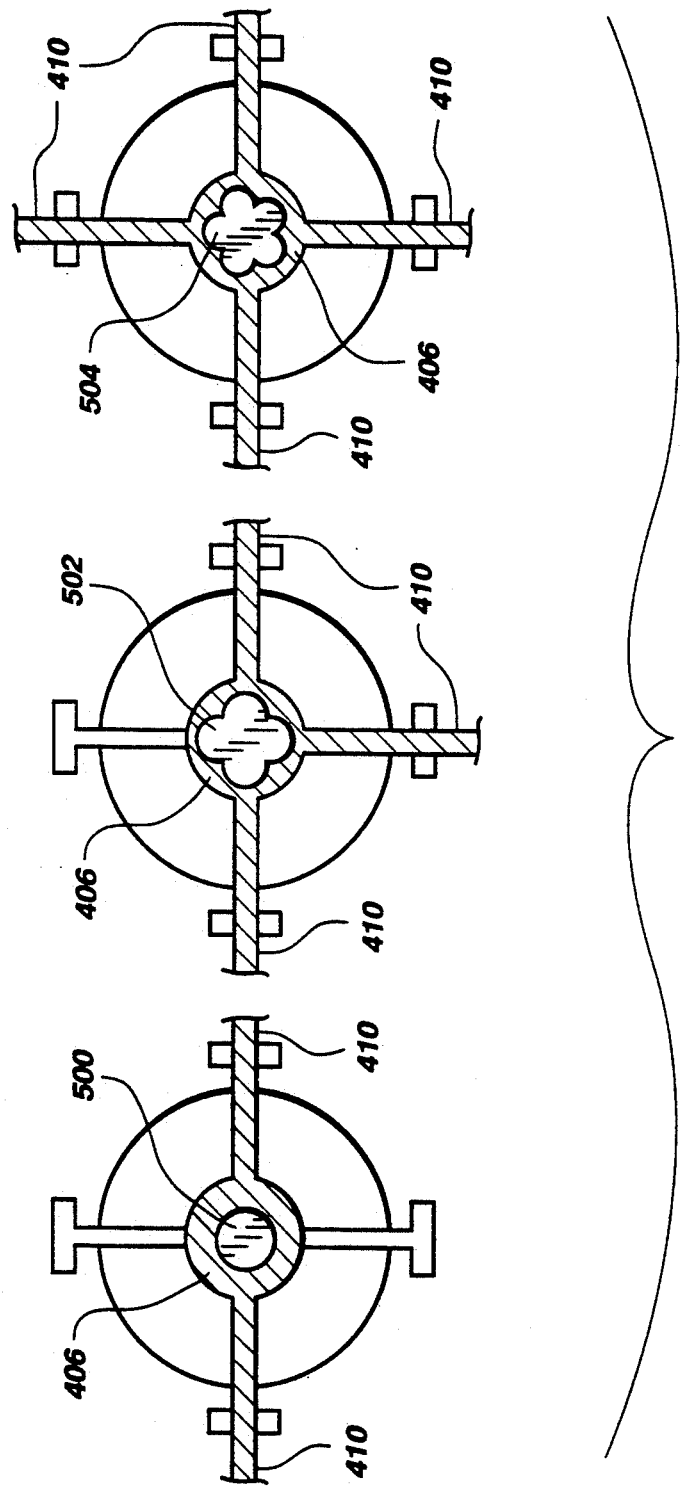
FIG. 5 contains cross-sectional views of mixers for generating binary, ternary, and quarternary solvent gradients.

FIGS. 4 and 5 depict a dynamic high pressure mixer which may be used as mixing unit 170 in FIG. 1. As shown in cross-section in FIG. 4, a motor 400 has a magnet bar 402 attached to the end of motor shaft 401. Motor 400 may be either a DC or an AC motor that has a constant rotation speed of about 100 RPM or higher. A housing 404 formed with an interior mixing chamber 406 is mechanically attached to a bracket 408. Motor 400 is also attached to bracket 408. Mixing chamber 406 is provided with inlet means comprising at least two inlets 410, 412 for connection to individual pumps to receive a different pressurized fluid from each. Outlet means comprising a single outlet 414 is provided for delivering pressurized mixed fluid from the mixer to an analytical unit. Outlet 414 includes an outlet filter 420 which is embedded inside the center core of a washer 422.

As motor shaft 401 rotates, magnetic bar 402 will induce rotation of a magnetic mixing bar 416 positioned within mixing chamber 406. The mixing bar 416 can be designed to various shapes and sizes for better mixing and smaller mixer volume.

Three identical sectional views of the mixer chamber 406 taken along line 5—5 are presented in FIG. 5, differing only in the number of inlets 410 which are receiving fluid as indicated by the hatched stream. Mixing bars 500, 502, 504 are shown having different shapes which may be advantageous for mixing of two, three, or four solvents, respectively, as indicated by the number of inlets 410 receiving fluid flow. The dimensions of mixing bars 500, 502, 504 may also be varied to effectively change the volume of fluid contained in mixer chamber 406.

Figure 6:
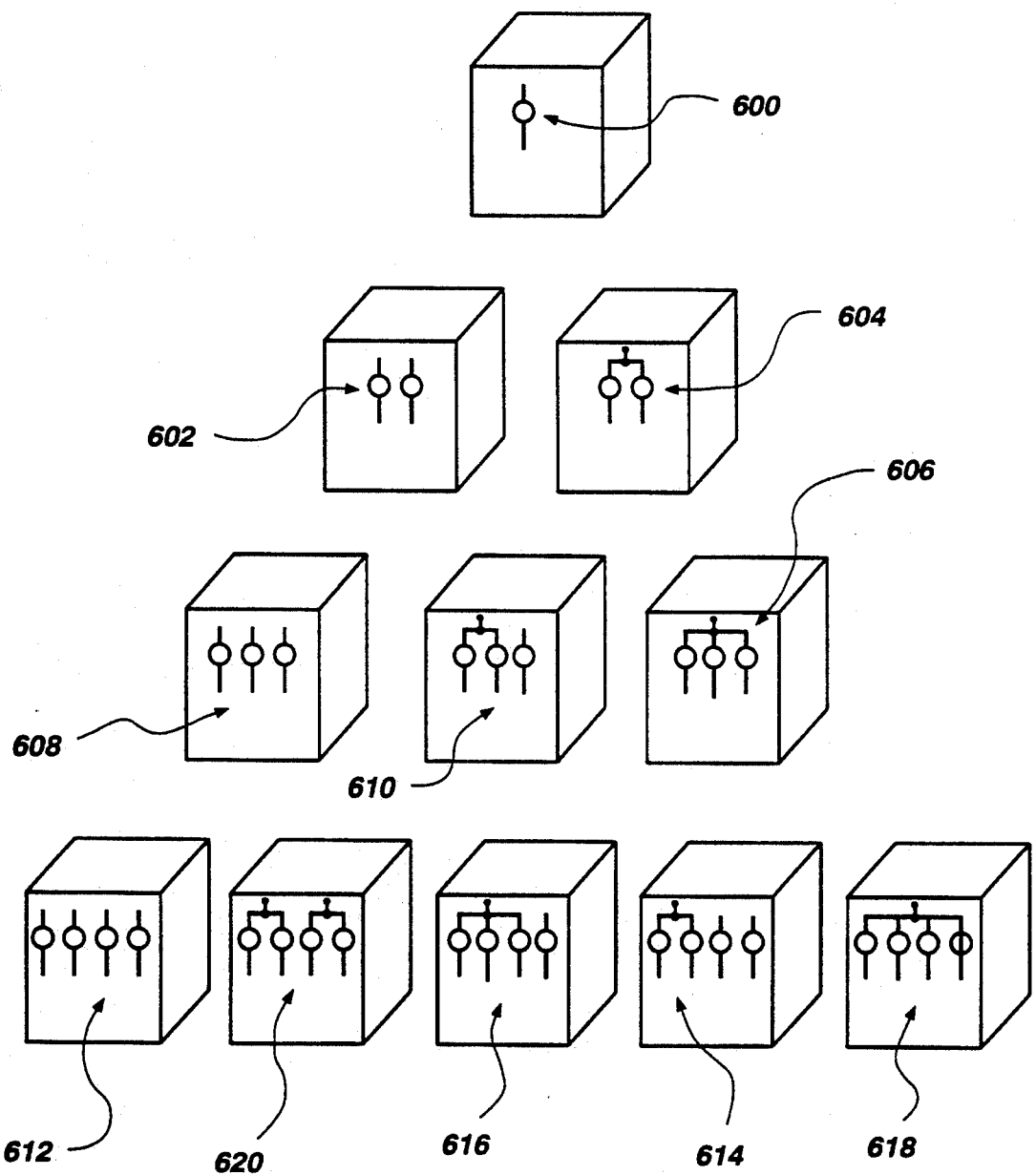
FIG. 6 is a simplified block diagram depicting a plurality of operating modes which can be performed with the multichannel pumping system of FIG. 1.

The operation modes possible with the pump system of FIG. 1 are illustrated in FIG. 6. A single pump pumping system 600 can be used as an isocratic pump for micro-HPLC, analytical-HPLC, and preparative-HPLC using piston and pump-head inner chamber sizes of 0.0625, 0.125, and 0.25 inch diameter, respectively. An additional pump can be mounted on the single pump system to become either a dual isocratic channel pump 602 or a binary solvent gradient pumping system 604. With a properly configured system controller, the dual pump-head pumping system can be used in both gradient and isocratic modes. A three-pump pumping system can be easily obtained by adding one additional pump to the dual pump system. A three-pump system can be operated as a ternary gradient 606, as three isocratic pumps 608, or as a combination of an isocratic and a binary gradient system 610. When a fourth pump is added, producing the embodiment of FIG. 1, the resulting quaternary pumping system can be operated in any of five modes. In isocratic mode 612, the four pump system can replace four isocratic pumps, pumping the same or different fluids. The coupling of two, three or four pumps allows operation in a single binary gradient mode 614, a ternary gradient mode 616, and a quaternary gradient mode 618. Provision of an additional mixer, and coupling two pumps each to the separate mixers, allows a dual independent binary gradient mode 620.

The number of individual pumps in one pumping system is not limited to four and thus even higher orders of gradient capability can be achieved.

From the above description, it will be apparent that the pumping system and the linear drive fluid pump of this invention have numerous advantages. Since the total liquid end volume of the pump including piston, inlet check valve, outlet check valve, pulse dampener, pressure transducer, and interface tubings is upstream of the proportioning and mixing unit, gradient linearity, gradient delay time, and gradient regeneration time are unaffected by a large liquid end volume.

Furthermore, the multi-channel pump system is capable of being operated as a multi-channel isocratic pump, or as binary, ternary, or quarternary gradient pumps. The pumping system including at least four individual pumps can be controlled from a single personal computer or the like. Constant flow rates in a range from about 0.0001 ml/minute to about 20 ml/minute at pressures of 10 to 10,000 psi are provided by the linear drive fluid pump having inter-changeable piston modules. A single multi-channel pump system including the invented fluid pump is thus useful for HPLC with microbore columns of I.D. $\leq 1$ mm, analytical columns which generally have an I.D. of between about 1 mm and 4.6 mm, and for preparative-scale-applications with columns of I.D. at least 10 mm. Preparative output potentially as large as 80 ml/minute is readily obtained by operating all four pumps at 20 ml/minute together as an isocratic pump. The latter preparative capacity is about eight times greater than that available with typical prior art HPLC apparatuses.

In addition to providing excellent flow rate control and range capacity, the linear drive fluid pump is extremely simple and durable. The design having a floating mount connecting the piston to the linear actuator, and the point contact between the motor coupling and the convex end of the piston, provide for self-aligning of the piston during operation which reduces wear and breakage thereof. The flex coupling to the linear actuator further reduces alignment problems and strain on key moving parts.

Although the multichannel pump system and the linear drive fluid pump are described primarily with reference to HPLC, their uses are not limited to HPLC and may include the following: super-critical fluid chromatography, supercritical fluid extraction, and capillary electrophoresis; or any other technology where multichannel high-pressure fluid delivery and/or accurate, low flow rates are desired.

What is claimed is:

1. A direct drive fluid pump, comprising:
   a central housing having first and second ends;
   a chamber housing mechanically attached to said central housing at said second end, and enclosing an elongated chamber having an opening at one end, an inlet including an inlet valve and connectable to receive fluid from an external reservoir, and an outlet including an outlet valve through which fluid may be expelled;
   a piston having a drive end and a pump end, said pump end being operably disposed for linear reciprocating motion in said chamber through said opening;
   a bidirectional motor having a motor shaft which rotates about an axis, said bidirectional motor mounted to said first end of said central housing; and
   drive coupling means mounted within said central housing for coupling said drive end of said piston to said motor shaft, said drive coupling means having a proximal portion comprising a rod having a first end and an externally threaded second end, said first end being mechanically affixed to said motor shaft for rotation in synchrony therewith about said axis, and a distal portion coupled to said drive end of said piston, said distal portion including mounting means disposed within and operably mounted to said central housing, for mounting said piston for slidable motion along the direction defined by said axis, said mounting means having an internally threaded cavity operably disposed and dimensioned for incremental and reversible engagement and rotation of said threaded second end of said rod, thereby to convert said rotation into linear reciprocating motion of said said piston;
   wherein said motor shaft and said piston are arranged substantially colinearly along said axis.

2. The fluid pump of claim 1 wherein said proximal portion of said coupling means is a ball screw and said distal portion includes a ball screw nut.

3. The fluid pump of claim 1, configured to provide pumping of said fluid at pressures ranging from zero to about 10,000 psi.

4. The fluid pump of claim 1, wherein said chamber and said piston are dimensioned, and said bidirectional motor is constructed to operate at a speed sufficient, to provide pumping rates between about 0.1 $\mu$l per minute and about 1200 $\mu$l per minute.

5. The fluid pump of claim 1 which outputs said fluid at a substantially constant rate.

6. The fluid pump of claim 1, further including floating coupling means for coupling said piston to said mounting means, said floating coupling means comprising:

a piston bracket mechanically affixed to said mounting means, said piston bracket having a piston attachment section displaced along said axis from, and out of direct contact with, said mounting means; and attachment means located on said piston attachment section for attaching said drive end of said piston.

7. The fluid pump of claim 6, wherein said inlet valve is a check valve and said outlet valve is a check valve.

8. The fluid pump of claim 6, wherein said attachment means is constructed for detachable attachment of said piston and said chamber housing is detachably affixed to said central housing, wherein said piston, said chamber housing and said chamber constitute a piston module and are dimensioned to provide a selected range of pumping capacities, said piston module being replaceable by an alternate piston module dimensioned to provide a different range of pumping capacities.

9. The fluid pump of claim 8, wherein said attachment means comprises an opening having a large portion and a smaller portion, and wherein said drive end of said piston is configured to pass freely through said large portion and to be detachably retained in said smaller portion.

10. The fluid pump of claim 9, wherein said drive end of said piston has a convex surface.

11. The fluid pump of claim 1, further including position determination means operably disposed with respect to said rod for determining a relative position of said externally threaded second end of said rod within said internally threaded cavity, said position determination means being constructed to provide a position signal output reflective of said relative position.

12. The fluid pump of claim 11, wherein said position determination means comprises a rotary encoder operably associated with said motor shaft for determining the amount of said rotation.

13. The fluid pump of claim 12, configured to pump said fluid at pressures ranging from about zero to about 10,000 psi.

14. The fluid pump of claim 12, wherein said chamber and said piston are dimensioned, and said bidirectional motor is constructed to operate at a speed sufficient, to provide pumping rates between about 0.1 $\mu$l per minute and about 1200 $\mu$l per minute.

15. The fluid pump of claim 12 wherein aid proximal portion of said coupling means is a ball screw and said distal portion includes a ball screw nut.

16. A fluid pump comprising:

a central housing having first and second ends;

a motor mounted to said first end of said central housing and having a motor shaft which provides rotary motion;

a piston unit comprising a chamber housing mechanically attached to said central housing at said second end, and enclosing a chamber having an opening at one end, an inlet including an inlet valve and connectable to receive fluid from an external reservoir, and an outlet including an outlet valve through which fluid may be expelled;

a piston having a drive end and a fluid end, said fluid end being slidably received within said chamber through said opening, floating coupling means attached to said drive end of said piston for coupling said piston to be reciprocated by said motor; and motor coupling means mounted within said central housing and connected between said motor and said piston coupling means for converting a rotary motion of said motor to a linear reciprocating motion of said piston, wherein said floating coupling means comprises a piston bracket mechanically affixed to said motor coupling means to be reciprocated thereby, said piston bracket having a piston attachment section and being configured and positioned to have said piston attachment section spaced along said axis from, and out of direct contact with, said motor coupling means, thereby creating a space between said distal end of said motor coupling means and said piston attachment section; and wherein said drive end of said piston is attached to said floating coupling means by means of coupling structure located on said piston attachment section.

17. The fluid pump of claim 16, wherein said coupling structure comprises an aperture in said piston attachment section, said drive end of said piston being configured to be slidably seated therein and further having collar means for retaining said drive end between piston attachment section and said motor coupling means.

18. The fluid pump of claim 17, wherein said drive end of said piston terminates in a convex surface.

19. The fluid pump of claim 17, wherein said drive end of said piston and said coupling structure are mutually configured for detachable attachment of said drive end to said traveling bracket.

20. The fluid pump of claim 19, wherein said aperture has a larger region and a smaller region, said larger region being dimensioned to allow said drive end of said piston to pass freely therethrough, and said smaller region is dimensioned to retain said collar means in said space.

* * * * *